(12) United States Patent
Vasan (10) Patent No.: US 11,547,823 B2
(45) Date of Patent: Jan. 10, 2023

(54) BOUGIE AND METHOD OF MAKING AND USING THE SAME

(71) Applicant: Nilesh R. Vasan, Oklahoma City, OK (US)

(72) Inventor: Nilesh R. Vasan, Oklahoma City, OK (US)

(*) Notice: Subject to any disclaimer, the term of this patent is extended or adjusted under 35 U.S.C. 154(b) by 374 days.

(21) Appl. No.: 14/251,296

(22) Filed: Apr. 11, 2014

(65) Prior Publication Data

US 2015/0290414 A1 Oct. 15, 2015

(51) Int. Cl.
*A61M 16/04* (2006.01)
*A61B 1/06* (2006.01)
*A61B 1/313* (2006.01)
*A61B 1/07* (2006.01)
*A61B 1/00* (2006.01)

(52) U.S. Cl.
CPC ..... *A61M 16/0488* (2013.01); *A61B 1/00032* (2013.01); *A61B 1/00135* (2013.01); *A61B 1/0684* (2013.01); *A61B 1/07* (2013.01); *A61B 1/3132* (2013.01); *A61M 2205/0205* (2013.01); *A61M 2205/32* (2013.01); *A61M 2205/3306* (2013.01); *A61M 2205/584* (2013.01); *A61M 2207/00* (2013.01)

(58) Field of Classification Search
CPC .. A61M 16/00; A61M 16/04; A61M 16/0402; A61M 16/0465–0497; A61M 25/00; A61M 25/06–0693; A61M 25/09–0905; A61M 29/00; A61M 29/02; A61M 2029/025; A61B 1/24; A61B 1/267–2676; A61B 17/34; A61B 2017/3454–346; A61B 1/32

USPC .................................................. 600/185–200
See application file for complete search history.

(56) References Cited

U.S. PATENT DOCUMENTS

| | | | | | |
|---|---|---|---|---|---|
| 4,502,482 | A | * | 3/1985 | DeLuccia | A61M 16/04 128/207.14 |
| 5,084,022 | A | * | 1/1992 | Claude | A61M 25/09 600/585 |
| 5,311,863 | A | * | 5/1994 | Toppses | A61M 16/04 128/207.14 |
| 6,010,520 | A | * | 1/2000 | Pattison | A61M 29/00 606/191 |

(Continued)

OTHER PUBLICATIONS

PCT/US2015/025345 PCT International Search Report and Written Opinion of the International Searching Authority, dated Jul. 27, 2015.

(Continued)

*Primary Examiner* — Samchuan C Yao (57) ABSTRACT

A bougie is disclosed with a body, and a first depth indicator and a second depth indicator on the body. The body has a first end, a second end, and at least one surface extending between the first and second ends. The first depth indicator is spaced a first distance from the first end and indicates a first predetermined depth range such that the first end is positioned a first predetermined insertion range past the mouth of the patient when the body is positioned into the mouth of the patient. The second depth indicator is spaced a second distance from the second end and indicates a second predetermined depth range such that the second end is positioned a second predetermined insertion range past the mouth when the body is positioned into the mouth of the patient.

18 Claims, 7 Drawing Sheets

(56) References Cited

U.S. PATENT DOCUMENTS

| | | | | |
|---|---|---|---|---|
| 6,463,927 | B1* | 10/2002 | Pagan | A61M 16/0488 128/200.26 |
| 7,650,886 | B1* | 1/2010 | Keller | A61M 16/0488 128/207.14 |
| 8,416,291 | B2* | 4/2013 | Carrey | A61B 1/00039 348/77 |
| D752,213 | S | 3/2016 | Paul et al. | |
| 2002/0066450 | A1 | 6/2002 | Bonutti | |
| 2003/0167065 | A1* | 9/2003 | Kumar | A61B 17/12022 606/158 |
| 2005/0137527 | A1 | 6/2005 | Kunin | |
| 2007/0129751 | A1 | 6/2007 | Muni | |
| 2007/0175482 | A1 | 8/2007 | Kimmel et al. | |
| 2008/0114303 | A1* | 5/2008 | Tremaglio | A61M 25/09 604/164.13 |
| 2009/0209826 | A1* | 8/2009 | Sanders | A61B 1/00082 600/188 |
| 2010/0217085 | A1* | 8/2010 | Williams et al. | A61B 1/267 600/193 |
| 2012/0029293 | A1 | 2/2012 | Vasan | |
| 2014/0230823 | A1* | 8/2014 | Adams | A61M 16/0488 128/207.14 |
| 2015/0034078 | A1 | 2/2015 | Sovndal | |

OTHER PUBLICATIONS

Extended European Search Report regarding EP Application No. 15776583.5, dated Dec. 19, 2017.
Examination Report No. 1 regarding Australian Patent Application No. 2015243274 dated Dec. 20, 2018.
Examination Report No. 1 regarding Indian Patent Application No. 201617034734 dated Mar. 11, 2020.
Examination Report No. 1 regarding Australian Patent Application No. 2019250237 dated Jul. 7, 2020.

* cited by examiner

BOUGIE AND METHOD OF MAKING AND USING THE SAME

BACKGROUND

A bougie is used to assist placement of an endotracheal tube in a patient's trachea to aid in oxygenation of the patient. The bougie is placed within the trachea of the patient as a guide over which a tube is passed. Often prior to procedures requiring anesthesia, a bougie is inserted between the vocal cords by a user using a laryngoscope. An endotracheal tube is passed over the bougie into the trachea of the patient. After placement of the endotracheal tube, the bougie is removed. Generally, the bougie is used in situations in which the endotracheal tube cannot be passed into the trachea directly or easily Bougies are generally formed from flexible materials, being either straight or curved. Some bougies are formed from self-lubricating materials such as the bougie described in U.S. Pat. No. 8,161,967, while others require a user to lubricate a surface of the bougie to insert the bougie into the trachea of the patient, such as the Sun-Med Bougie Introducer™ (Sun-Med™ Largo, Fla., USA.).

A laryngoscope may be used to assist with the placement of a tube into a patient's trachea to aid with the oxygenation of the patient. The laryngoscopes often use either a straight or curved blade that allows for the visualization of the patient's vocal cords which are used for locating the patient's larynx and subsequently the trachea. This reduces the risk of intubating the patient's esophagus which would cause air to be blown into the stomach, causing stomach distension and vomiting not to mention depriving the patient of oxygen, and possibly death.

The presence of blood, saliva, and vomit secretions can interfere with the proper placement of the laryngoscope, further necessitating the use of the bougie. Further, in emergency situations, the proper placement of the laryngoscope must be done in a quick and safe manner. Often determining a proper depth of insertion for a bougie may be difficult, for example in emergency situations or in the presence of obscuring fluids or objects. Despite good technique by the health care provider utilizing the bougie, there is still a need for an improved bougie that can be used in difficult or emergency situations in and out of a medical facility while being reliably positioned at a proper insertion depth.

SUMMARY OF THE INVENTION

In one version, a bougie is described as having a body, a first depth indicator on the body, and a second depth indicator on the body. The body has a first end and a second end, being blunted, and at least one surface extending between the first and second ends. The body has an elongated shape that is sized and dimensioned to pass through a mouth and into a trachea of a patient. The body is constructed of a flexible and non-immunogenic material. The first depth indicator is spaced a distance from the first end of the body and configured to indicate a first predetermined depth range such that the first end of the body is positioned a first predetermined insertion range past the mouth of the patient or proximal end of the laryngoscope that is within the patients mouth when the body is positioned into the mouth of the patient with the first depth indicator. The second depth indicator is spaced a second distance from the second end of the body and configured to indicate a second predetermined depth range such that the second end of the body is positioned a second predetermined insertion range past the mouth of the patient or proximal end of the laryngoscope that is within the patients mouth when the body is positioned into the mouth of the patient with the second depth indicator. The first predetermined depth range and the second predetermined depth range are different.

In another version a method of making a bougie is disclosed and performed by forming a bougie having a body, a first depth indicator on the body, and a second depth indicator on the body. The body has a first end, a second end, and at least one surface extending between the first and second ends. The first and second ends are blunted. The first depth indicator is spaced a first distance from the first end of the body and configured to indicate a first predetermined depth range such that the first end of the body is positioned a first predetermined insertion range past the mouth of a patient when the body is positioned in a mouth of the patient or proximal end of the laryngoscope that is within the patients mouth. The second depth indicator is spaced a second distance from the second end of the body and configured to indicate a second predetermined depth range such that the second end of the body is positioned a second predetermined insertion range past the mouth of the patient or proximal end of the laryngoscope that is within the patients mouth when the body is positioned into the mouth of the patient with the second depth indicator. The first predetermined depth range is different from the second predetermined depth range.

In another embodiment, a method of making a bougie is disclosed and performed by forming a first depth indicator on a body of the bougie. The body of the bougie has a first end and a second end, being blunted, and at least one surface extending between the first and second ends. The body has an elongated shape that is sized and dimensioned to pass through a mouth and into a trachea of a patient. The body is constructed of a flexible and non-immunogenic material. The first depth indicator is formed on the body and spaced a first distance from the first end of the body and configured to indicate a first predetermined depth range such that the first end of the body is positioned a first predetermined insertion range past the mouth of the patient when the body is positioned into the mouth of the patient with the first depth indicator. The method is further performed by forming a second depth indicator on the body of the bougie, the second depth indicator spaced a second distance from the second end of the body and configured to indicate a second predetermined depth range such that the second end of the body is positioned a second predetermined insertion range past the mouth of the patient when the body is positioned into the mouth of the patient with the second depth indicator. The first predetermined depth range is different from the second predetermined depth range.

In another version, a method of use for a bougie is disclosed and performed by obtaining a bougie. The bougie having a body with a first depth indicator spaced a distance from a first end of the body and configured to indicate a first predetermined insertion range. The body also has a second depth indicator spaced a second distance from a second end of the body and is configured to indicate a second predetermined insertion range. The method is further performed by determining whether the first predetermined insertion range or the second predetermined insertion range is appropriate for a particular patient. The method is then further performed by performing at least one of the following actions: inserting the first end of the body into a mouth of the patient responsive to the determination that the first predetermined insertion range is appropriate for the particular patient; and inserting the second end of the body into the mouth of the patient responsive to a determination that the second predetermined insertion range is appropriate for a particular patient.

In another version, a kit is disclosed. The kit is described as including a bougie and a laryngoscope as well as other possible equipment such as suction or instruments that could be used through the laryngoscope. The bougie has a body, a first depth indicator on the body, and a second depth indicator on the body. The body of the bougie has a first end and a second end, being blunted, and at least one surface extending between the first and second ends. The body has an elongated shape that is sized and dimensioned to pass through a mouth and into a trachea of a patient. The body is constructed of a flexible and non-immunogenic material. The first depth indicator is spaced a first distance from the first end of the body and configured to indicate a first predetermined depth range such that the first end of the body is positioned a first predetermined insertion range past the mouth of the patient when the body is positioned into the mouth of the patient with the first depth indicator. The second depth indicator is spaced a second distance from the second end of the body and configured to indicate a second predetermined depth range such that the second end of the body is positioned a second predetermined insertion range past the mouth of the patient when the body is positioned into the mouth of the patient with the second depth indicator. The first predetermined depth range and the second predetermined depth range are different. The laryngoscope has a handle, a tube coupled to the handle, and an optical subassembly providing light to the tube. The tube is constructed of a translucent material and has a proximal end, which is coupled to the handle, a distal end including a distal opening, and an interior extending from the proximal end of the distal end. The optical subassembly provides light to the interior of the tube so that a first portion of the light exits the interior of the tube via the distal opening and a second portion of the light propagates into the translucent material to illuminate the tube.

Upon reading the included description, various alternative embodiments will become obvious to those skilled in the art. These embodiments are to be considered within the scope and spirit of the subject disclosure, which is only limited by the claims which follow and their equivalents.

BRIEF DESCRIPTION OF THE DRAWINGS

Certain embodiments of the inventive concepts will hereafter be described with reference to the accompanying drawings, wherein like reference numerals denote like elements. It should be understood, however, that the accompanying figures illustrate the various implementations described herein and are not meant to limit the scope of the various technologies described herein.

FIGS. 3-1-3-5 show a method of using the bougie of FIG. 1:

FIG. 3-1 is a partial cross sectional diagram of obtaining the bougie and determining whether a first predetermined insertion range or a second predetermined insertion range is appropriate for the patient;

FIG. 3-2 is a partial cross sectional diagram of inserting the bougie, of FIG. 3-1, into a trachea of the patient;

FIG. 3-3 is a partial cross sectional diagram of inserting an endotracheal tube into the trachea of the patient around the bougie of FIG. 3-1;

FIG. 3-4 is a partial cross sectional diagram of positioning the endotracheal tube, of FIG. 3-4, into the trachea of the patient; and FIG. 3-5 is a partial cross sectional diagram of removing the bougie, of FIG. 3-1, from the trachea of the patient.

FIG. 5-1 is an exploded view of another embodiment of the laryngoscope of FIG. 5.

FIG. 5-2 is a partial diagram of another embodiment of the laryngoscope of FIG. 5.

DETAILED DESCRIPTION

Specific embodiments of the present disclosure will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited or inherently present therein.

As used herein any references to "one embodiment" or "an embodiment" means that a particular element, feature, structure, or characteristic described in connection with the embodiment is included in at least one embodiment. The appearances of the phrase "in one embodiment" in various places in the specification may not refer to the same embodiment.

The present disclosure is generally directed toward a bougie, more specifically, toward a bougie having a body with a plurality of depth indicators configured to indicate a plurality of depth ranges such that the body may be positioned at one of a plurality of predetermined insertion ranges past the mouth of a patient when the body of the bougie is positioned into a mouth of the patient via an instrument such as a laryngoscope with one of the plurality of depth indicators.

Figure 1:
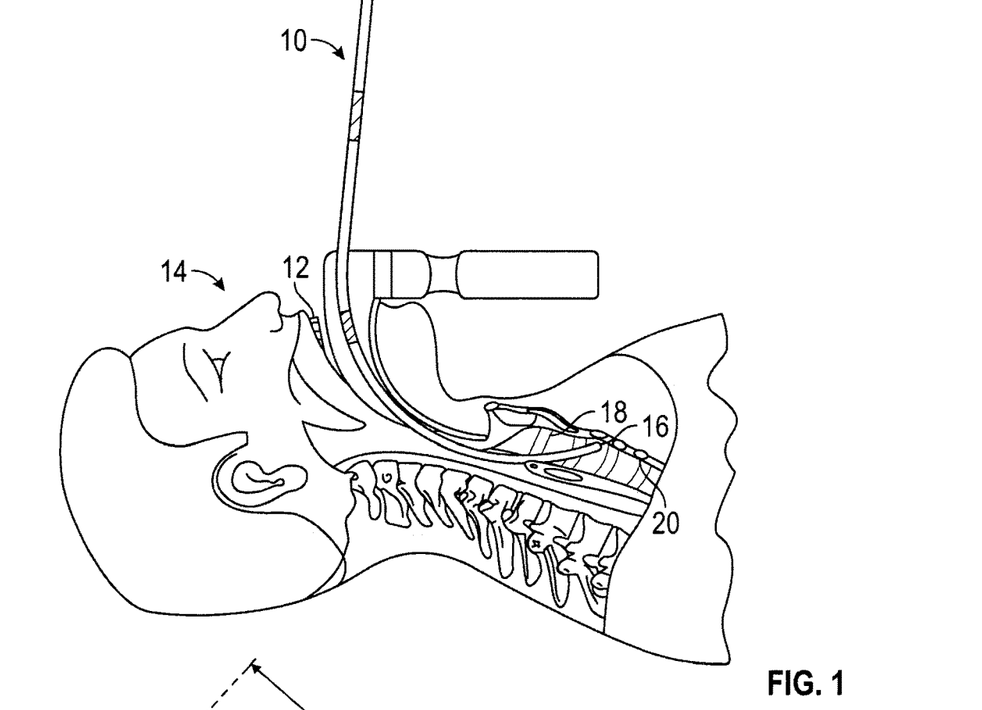
FIG. 1 is a partial cross sectional view of a bougie inserted into a trachea of a patient, in accordance with some embodiments of the present disclosure.

Referring now to FIG. 1, shown therein is a bougie 10, also referred to as an introducer, inserted into a mouth 12 of a patient 14 with a first end 16 of the bougie 10 positioned past a vocal cord 18, housed in a larynx and hereinafter referred to interchangeably as the larynx 18, of the patient 14 and within a trachea 20 of the patient 14.

Figure 2:
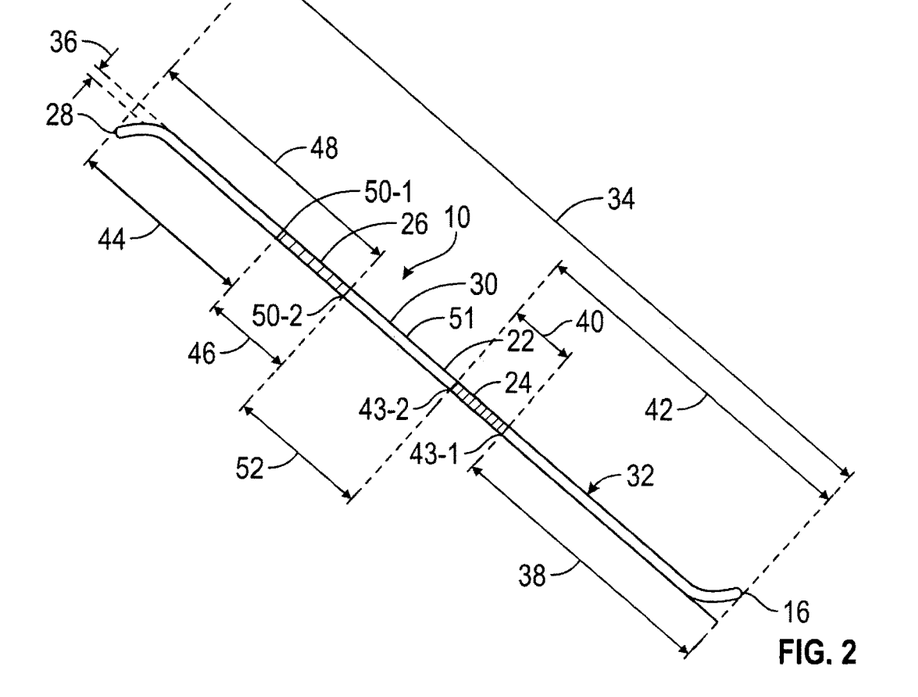
FIG. 2 is a side view of the bougie of FIG. 1, in accordance with some embodiments of the present disclosure.

Referring now to FIGS. 1 and 2, the bougie 10 may be provided with a body 22, a first depth indicator 24 on the body 22, and a second depth indicator 26 on the body 22. The body 22 may be provided with the first end 16, a second end 28, and at least one surface 30 extending between the first and second ends 16 and 28. The body 22 may be provided with an elongated shape 32 that may be sized and dimensioned to pass through the mouth 12 and into the trachea 20 of the patient 14. The elongate shape 32 of the body 22 may have a length 34 extending between the first and second ends 16 and 28 and a width 36 extending substantially perpendicularly to the length 34, where the width 36 is less than the length 34. For example, in some embodiments, the length 34 may be in a range between about 60 cm and about 70 cm. The width 36, or in some embodiments the diameter, of the cross section may be in a range of between about 0.3 cm to about 0.7 cm or a range of between about 8-20 Fr, for example. In some embodiments, the body 22 may have a circular, an ovaline, a polygonal, or any other suitable cross sectional shape. In embodiments where the body 22 has a polygonal cross section, each of a plurality of vertices on the surface 30 of the body 22 may be blunted to prevent trauma to the patient 14.

In some embodiments, the first end 16, the second end 28, or both may be blunted, such that passing the first end 16 or the second end 28 into the mouth 12, past the larynx 18, and into the trachea 20 of the patient 14 may not cause trauma to the mouth 12, the vocal cords 18, or the trachea 20 of the patient 14. In some embodiments, the first end 16 and the second end 28, or both the first and second ends 16 and 28 may be formed at an angle with respect to the body 22 of the bougie 10, as shown in FIG. 2. In these embodiments, the first end 16, the second end 28, or both may be angled so as to approximate a natural curvature of a throat extending between the mouth 12 and the trachea 20 of the patient 14.

The body 22 may be constructed from a flexible and non-immunogenic material. For example, the body 22 may be constructed from Teflon™ (available from DuPont™, Wilmington, Del., U.S.A.), polytetrafluoroethylene, polyethylene terephthalate (PET), polyvinyl chloride (PVC), polyethylene (PE), polybutylene terephthalate (PBT), plastic, Silastic® (available from Dow Corning®, Midland, Mich., U.S.A.), cork, rubber, metal, or any other suitable material. In some embodiments, the body 22 may be formed from a braided material, such as braided polyester. In some of these embodiments, the braided material may be coated, for example with a resin or plastic.

The first depth indicator 24 may be on the body 22 of the bougie 10 and be spaced a first distance 38 from the first end 16 of the body 22. The first depth indicator 24 may be configured to indicate a first predetermined depth range 40 such that the first end 16 of the body 22 is positioned a first predetermined insertion range 42 past the mouth 12 of the patient 14 when the body 22 is positioned in the mouth 12 of the patient 14 with the first depth indicator 24. When inserted through a laryngoscope, the first end 16 of the body 22 may also be inserted past a proximal end of the laryngoscope when the body 22 is positioned in the mouth 12 of the patient 14 with the first depth indicator 24. In some embodiments, the first depth indicator 24 may have a first end 43-1 and a second end 43-2. The first end 16 may be positioned past the vocal cords 18 of the patient 14 when the first depth indicator is positioned in the mouth 12 of the patient 14. The first end 43-1 may be indicative of approximately a minimum insertion depth of the first predetermined insertion range 42. The second end 43-2 may be indicative of approximately a maximum insertion depth of the first predetermined insertion range 42. In some embodiments, as will be explained below in more detail, the first predetermined insertion range 42 may be a distance from the mouth 12 of the patient 14 to an area within the trachea 20 of the patient 14 at which the first end 16 of the bougie 10 may be positioned for the bougie 10 to aid in intubation of the patient 14 while preventing over-extension of the first end 16 beyond the trachea and bronchus/lung injury. In some embodiments, the first depth indicator 24 may extend along the body 22 of the bougie 10 a distance between about 5 cm to about 7 cm between the first end 43-1 and the second end 43-2 of the first depth indicator 24.

In some embodiments, the first depth indicator 24 between about 5 cm and about 15 cm in length. The first depth indicator 24 may be integral to the body 22 of the bougie 10 and formed as a raised section, such as a single raised section, or a series of spaced apart rings extending a distance between the first and second ends 16 and 28 of the body 22. The first depth indicator 24 may also be formed as a lowered section or otherwise textured section, or plurality of lowered or textured sections extending a distance between the first and second ends 16 and 28 of the body 22. In some other embodiments, the first depth indicator 24 may be connected to the body 22 of the bougie 10 after the body 22 has been formed.

In some embodiments, the first depth indicator 24 may be a colored section or a plurality of colored sections extending a distance between the first and second ends 16 and 28 of the body 22. In embodiments where the first indicator 24 is a colored section or plurality of colored sections, the first indicator 24 may be integral to the body 22 of the bougie 10, formed contemporaneously with the body 22, or may be formed on at least one surface 30 of the body 22 of the bougie 10. For example, in some embodiments, the first indicator 24 may be formed from a paint, dye, stain, glow in the dark coloring, ultraviolet light sensitive coloring, a radiopaque coloring or coating, or other permanent or semi-permanent marking material applied to the at least one surface 30 of the body 22. In some embodiments, similar to those described for the colored sections, the first depth indicator 24 may be formed from text. For example conveying an appropriate range for the first predetermined depth range 40, such as "start" at the first end 43-1 of the first depth indicator 24 and "end" at the second end 43-2 of the first depth indicator 24. In some embodiments, a combination of text and graphical indicators may be used to form the first depth indicator 24. For example, the first end 43-1 and the second end 43-2 may be formed from graphics or lines and text, such as the word "safe" or "go" may be formed on the at least one surface 30 and extend at least a portion of the distance between the first end 43-1 and the second end 43-2. In some embodiments, the first depth indicator 24 may be formed from a combination of the raised section, lowered section, textured section, colored section, or pluralities of the same.

The first distance 38 may be a distance between the first end 16 of the body and the first end 43-1 of the first depth indicator 24. In general, the first distance 38 may be measured such that insertion of the first end 16 of the bougie 10 into the mouth 12 of the patient 14 to the first end 43-1 of the first depth indicator 24 may be equal to a minimum average insertion depth within the first predetermined insertion range 42, where the minimum average insertion depth is representative of a low end of the first predetermined insertion range 42. Similarly, inserting the first end 16 of the bougie 10 into the mouth 12 of the patient 14 to the second end 43-1 of the first depth indicator 24 may be equal to a maximum average insertion depth within the first predetermined insertion range 42, where the maximum average insertion depth is representative of a high end of the first predetermined insertion range 42. For example, in some embodiments, the first distance 38 may be in a range from about 13 cm to about 23 cm. The first predetermined depth range 40 may be sized for insertion into the mouth 12 of the patient 14 of a first predetermined age range. For example, the first predetermined depth range 40 may be about 10 cm and the first predetermined age range may be between about 10 and about 100 years of age.

As indicated above, the first predetermined insertion range 42 may be a distance from the mouth 12 of the patient 14 to an area within the trachea 20 of the patient 14 at which the first end 16 of the bougie 10 may be positioned for the bougie 10 to aid in intubation of the patient 14 while preventing over-extension of the first end 16 and lung injury. For example, the first predetermined insertion range 42 may be a range for an averaged subset of patients 14 within a group of all possible patients 14. The first predetermined insertion range 42 may be in part determined based on the first predetermined age range of the patient 14. It should be understood that the bougie 10 should be inserted to differing insertion ranges where the patient 14 is an adult than if the patient 14 were a child. In at least some embodiments, the first predetermined insertion range 42 may be between about 23 cm and about 33 cm for patients in the first predetermined age range.

The second depth indicator 26 may be on the body 22 of the bougie 10 and be spaced a second distance 44 from the second end 28 of the body 22. The second depth indicator 26 may be configured to indicate a second predetermined depth range 46 such that the second end 28 of the body 22 is positioned a second predetermined insertion range 48 past the mouth 12 of the patient 14 when the body 22 is positioned in the mouth 12 of the patient 14 with the second depth indicator 26. The second end 28 may be positioned past the vocal cords 18 of the patient 14 when the second depth indicator 26 is positioned in the mouth 12 of the patient 14. In some embodiments, the second depth indicator 26 may have a first end 50-1 and a second end 50-2. The first end 50-1 may be indicative of approximately a minimum insertion depth of the second predetermined insertion range 48. The second end 50-2 may be indicative of approximately a maximum insertion depth of the second predetermined insertion range 48. In some embodiments, the second depth indicator 26 may extend along the body 22 of the bougie 10 a distance between about 5 cm to about 15 cm between the first end 50-1 and the second end 50-2 of the second depth indicator 26.

In some embodiments, the second depth indicator 26 may be integral to the body 22 of the bougie 10 and formed as a raised section, a lowered section or otherwise textured section, or a plurality of lowered or textured sections similar to the first depth indicator 24. In some embodiments, the second depth indicator 26 may be a colored section; a text section; a graphical and text section; or a plurality of colored, text, or combination graphical and text sections similar to the first depth indicator 26. The second depth indicator 26 may also, in some embodiments, a combination of the above described raised sections, lowered sections, textured sections, colored sections, and/or text, similar to the first depth indicator 24 described above. In some embodiments, the second depth indicator 26 may also be connected to or applied to the body 22 of the bougie 10 after the bougie 10 has been formed.

In some embodiments, the second depth indicator 26 may be implemented in such a manner as to be visually and/or tactilely distinct from the first depth indicator 24. For example, the first depth indicator 24 may be formed from a plurality of raised sections, such as a plurality of spaced apart rings, and the second depth indicator 26 may be formed from a textured section, without the plurality of spaced apart rings. By way of a further example, in embodiments where the first and second depth indicators 24 and 26 are implemented as colored sections, the first and second depth indicators 24 and 26 may be differentially colored. For example, the first depth indicator 24 may be formed from a purple color and the second depth indicator 26 may be formed from a green color. In some embodiments, the first and second depth indicators 24 and 26 may be differentiated by distinct text sections, such as text on the first depth indicator 24 indicating a first predetermined age range and text on the second depth indicator 26 indicating a second predetermined age range.

The second distance 44 may be a distance between the second end 28 of the body 22 and the first end 50-1 of the second depth indicator 26. The second distance 44 may be measured such that insertion of the second end 28 of the bougie 10 into the mouth 12 of the patient 14 to the first end 50-1 of the second depth indicator 26 may be equal to a minimum average insertion depth within the second predetermined insertion range 48. The minimum average insertion depth may be representative of a low end of the second predetermined insertion range 48. Similarly, inserting the second end 28 of the bougie 10 into the mouth 12 of the patient 14 to the second end 50-2 of the second depth indicator 26 may be equal to a maximum average insertion depth within the second predetermined insertion range 48. The maximum average insertion depth may be representative of a high end of the second predetermined insertion range 48. In some embodiments, the second distance 44 may be equal to the first distance 38, for example in a range from about 13 cm to about 23 cm. The second predetermined depth range 46 may be sized for insertion into the mouth 12 of the patient 14 of a second predetermined age range. In some embodiments, the second predetermined age range may be the same as the first predetermined age range, for example between about 10 and about 100 years of age.

In some embodiments the second predetermined age range may be different from the first predetermined age range, and fall outside of or within a subsection of the 10 to 100 year age range. For example, the second predetermined age range may be from 0 to 10 years or from 5 to 10 years, or any other suitable age range. In these embodiments, the second depth indicator 26 may be configured, for example, for use in pediatric patients and the first depth indicator 24 may be configured for use in adult patients. In these embodiments, the second distance 44 may be different from the first distance 38, and in at least some embodiments, the second distance 44 may be less than the first distance 38. Where the second depth indicator 26 is configured for a different age range of patients from the first depth indicator 24, the second depth indicator 26 may be additionally differentiated from the first depth indicator 24 by colorings, markings, text, shape, texture, or other suitable manner in order to assist a user in determining whether to use the first depth indicator 24 or the second depth indicator 26 on the patient 14.

As discussed above with respect to the first predetermined insertion range 42, the second predetermined insertion range 48 may be a distance from the mouth 12 of the patient 14 to an area within the trachea 20 of the patient 14 at which the second end 28 of the bougie 10 may be positioned for the bougie 10 to aid in intubation of the patient 14 while preventing over-extension of the second end 28 and lung injury. The second predetermined insertion range 48 may be a range for an averaged subset of patients 14 within a group of all possible patients 14, and may be in part determined based on the second predetermined age range of the patient 14. In at least some embodiments, the second predetermined insertion range 48 may be the same as the first predetermined insertion range 42, for example between about 23 cm and about 33 cm for the patient 14 in the second predetermined age range. In some embodiments, the second predetermined insertion range 48 may differ from the first predetermined insertion range 42, for example, where the second depth indicator 26 is configured to be used on pediatric patients and the first depth indicator 24 is configured to be used on adult patients. In these embodiments, the second predetermined insertion range 48 may be longer or shorter than the first predetermined insertion range 42 and be of a length suitable for use with patients in the second predetermined age range.

In some embodiments, the first depth indicator 24 and the second depth indicator 26 may be first and second depth indicators of a plurality of depth indicators. For example, each of the first and second depth indicators 24 and 26 may be divided into a plurality of depth indicators with contrasting areas indicative of discrete measurements of the first and second predetermined insertion ranges 42 and 48, respectively. By way of further example, the contrasting areas, tick marks, differing textures, or other indicators may indicate increasing depth of the first and second predetermined insertion ranges 42 and 48 in centimeter increments.

In some embodiments, where the first and second depth indicators 24 and 26 are first and second depth indicators of the plurality of depth indicators, the bougie 10 may include a third depth indicator 51 which may be used to indicate an unsafe insertion depth of either the first end 16 or the second end 28 of the bougie 10. The third depth indicator 51 may extend between the first and second depth indicators 24 and 26 along the body 22 of the bougie 10. For example, the third depth indicator 51 may extend a length 52 between the second end 43-1 of the first depth indicator 24 and the second end 50-2 of the second depth indicator 26. In some embodiments, the length 52 may be between about 4 cm and about 14 cm. The length 52 of the third depth indicator 51 may depend on the length 34 of the bougie 10, the length of the first depth indicator 24, the length of the second depth indicator 26, the first predetermined insertion range 42, and/or the second predetermined insertion range 48. The third depth indicator 51 may formed similarly to the first and second depth indicators 24 and 26, and may be formed in a manner so as to differentiate the third depth indicator 51 from the first and second depth indicators 24 and 26. For example, the third depth indicator 51 may be formed from a differing color than the first and second depth indicators 24 and 26; may have text indicating unsafe insertion, such as "unsafe" or "stop"; may have a texture or physical configuration differing from the first and second depth indicators 24 and 26; or combinations thereof. By way of further example, the first and second depth indicators 24 and 26 may be colored green while the third depth indicator 51 may be colored red.

In some embodiments, the bougie 10 may be configured for a single use and to be disposed after that use by being made of a material that cannot be disinfected reliably after use. Examples of such materials include cork, some plastics, some rubbers, and other suitable materials. In some embodiments, the bougie 10 is configured to be reusable. In these embodiments, the bougie 10 may be disinfected after use on the patient 14, prior to being used in another patient.

In some embodiments, the bougie 10 may be formed via injection molding, 3-D printing, molding, extrusion, thermoforming, casting, and other suitable processes. In some embodiments, the bougie 10 may be made by a method performed by forming the bougie 10 having the body 22, the first depth indicator 24 on the body 22, and the second depth indicator 26 on the body 22. In these embodiments, the first and second depth indicators 24 and 26 are formed contemporaneously to the body 22 of the bougie 10. The first and second depth indicators 24 and 26 and the body 22 of the bougie 10 may be implemented as described above.

In some embodiments, the bougie 10 may be made by a method performed by forming the first depth indicator 24 on the body 22 of the bougie 10 spaced the first distance 38 from the first end 16 of the body 22, and forming the second depth indicator 26 on the body 22 of the bougie 10 spaced the second distance 44 from the second end 28 of the body 22. In some embodiments, the first and second depth indicators 24 and 26 may be formed on the body 22 of the bougie 10 after the body 22 of the bougie 10 has been formed. In some embodiments, the first depth indicator 24 may be formed on the body 22 of the bougie 10 prior to the second depth indicator 26 being formed or vice versa. In some other embodiments, the second depth indicator 26 may be formed on the body 22 of the bougie 10 at a time substantially contemporaneous with the first depth indicator 26. The first depth indicator 24, the second depth indicator 26, and the body 22 of the bougie 10 may be implemented similarly or the same as described above.

Referring now to FIGS. 3-1-3-5, in use, the bougie 10 may be used by a user inserting a laryngoscope 55 into the mouth 12 of the patient 14 to visualize the vocal cords 18, as shown in FIG. 3-1. The method is further performed by the user obtaining the bougie 10, and determining whether the first predetermined insertion range 42 or the second predetermined insertion range 48 is appropriate for a particular patient, such as the patient 14. After determining whether the first or second predetermined insertion range 42 or 48 is appropriate, the method may further be performed by performing at least one of the following actions. The first end 16 of the body 22 may be inserted into the mouth 12 of the patient 14 responsive to the determination that the first predetermined insertion range 42 is appropriate for the particular patient 14, as shown in FIG. 3-2. The second end 28 of the body 22 may be inserted into the mouth 12 of the patient 14 responsive to the determination that the second predetermined insertion range 48 is appropriate for the particular patient 14. In some embodiments, the insertion range for the patient 14 may be determined by an age range of the patient 14. As noted above, determining which of the first and second predetermined insertion ranges 42 and 48 corresponds to the insertion range may be based on the first predetermined age range for the first predetermined insertion range 42 and the second predetermined age range for the second predetermined insertion range 48.

After inserting either the first or second end 16 or 28 of the body 22 into the mouth 12 of the patient 14, the first or second end 16 or 28 may be passed through the mouth 12 of the patient 14 and past the vocal cords 18 of the patient 14, as shown in FIG. 3-2. The user may determine the insertion depth of the first or second end 16 or 28 the first or second depth indicator 24 or 26, respectively. Additionally, the user may verify the insertion depth by tactile feedback from the first or second end 16 or 28 contacting one or more of a plurality of tracheal rings 54. After the bougie 10 has been inserted into the trachea 20 of the patient 14, the laryngoscope 55 may be removed and the bougie 10 left in place. In some embodiments, after insertion of the bougie 10 into the trachea 20 of the patient 14 and removal of the laryngoscope 55, an endotracheal tube 56 may be extended into the trachea 20 of the patient 14 around the bougie 10, as shown in FIG. 3-3. The endotracheal tube 56 may then be positioned such that a first end 58 of the endotracheal tube 56 is positioned in the trachea 20 of the patient 14, as shown in FIG. 3-4. In these embodiments, the bougie 10 may be removed after placement of the endotracheal tube 56, as shown in FIG. 3-5.

Figure 4:
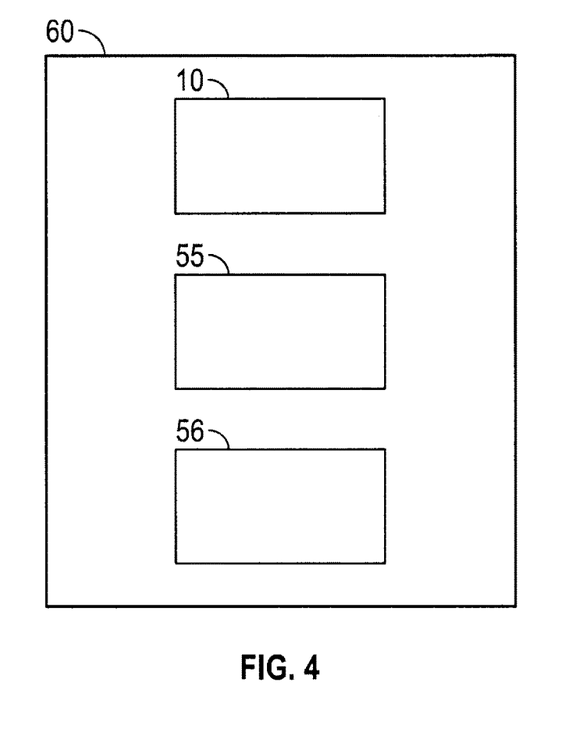
FIG. 4 is a diagrammatic representation of a kit in accordance with the present disclosure.

Referring now to FIG. 4, in some embodiments, the bougie 10 may be provided in a kit 60. The kit 60 may include the bougie 10, implemented as described above, and the laryngoscope 55. The bougie 10, included in the kit 60, may be packaged in a curled, wound, or otherwise collapsed form to save space within packaging for the kit 60 and extend to the length described above once removed from the packaging. In some embodiments, the bougie 10 may be curled, wound, or otherwise collapsed and packaged in a size and configuration sufficient to be stored in a pocket, for example.

As shown, in some embodiments, as shown in FIG. 4, the kit 60 may include the bougie 10, the laryngoscope 55 and the endotracheal tube 56. In some embodiments, the kit 60 may be provided in a container 63, such as a box, a disposable box, a bag, a disposable bag, or other suitable container. The container 63 may keep the bougie 10, the laryngoscope 55, and the endotracheal tube 56 together for use in emergency situations, or other appropriate instants of use. For example, the container 63 may contain the kit 60 in supply rooms of hospitals or clinics, ambulances, or other suitable locations.

In some embodiments, the kit 60 may additionally include one or more suction catheter, and/or one or more tools or instruments for manipulating the larynx. For example, the kit 60 may include a rigid suction instrument, capable of reaching beyond the length of the laryngoscope 55; grasping forceps, capable of reaching beyond the length of the laryngoscope 55 to dislodge a foreign body within the throat or take a biopsy of the larynx, pharynx or trachea 20 or other areas of the upper aerodigestive tract; a rigid angled hook, capable of reaching beyond the length of the laryngoscope 55 to dislodge a foreign body within the trachea 20; the laryngoscope 55 with side channel ventilation ports to allow ventilation of the patient 14 through the laryngoscope 55; the endotracheal tube 56; and/or other suitable instruments and/or tools. The instruments included in the kit 60 may be formed from metal, plastics, or any of the materials discussed above or below.

Figure 5:
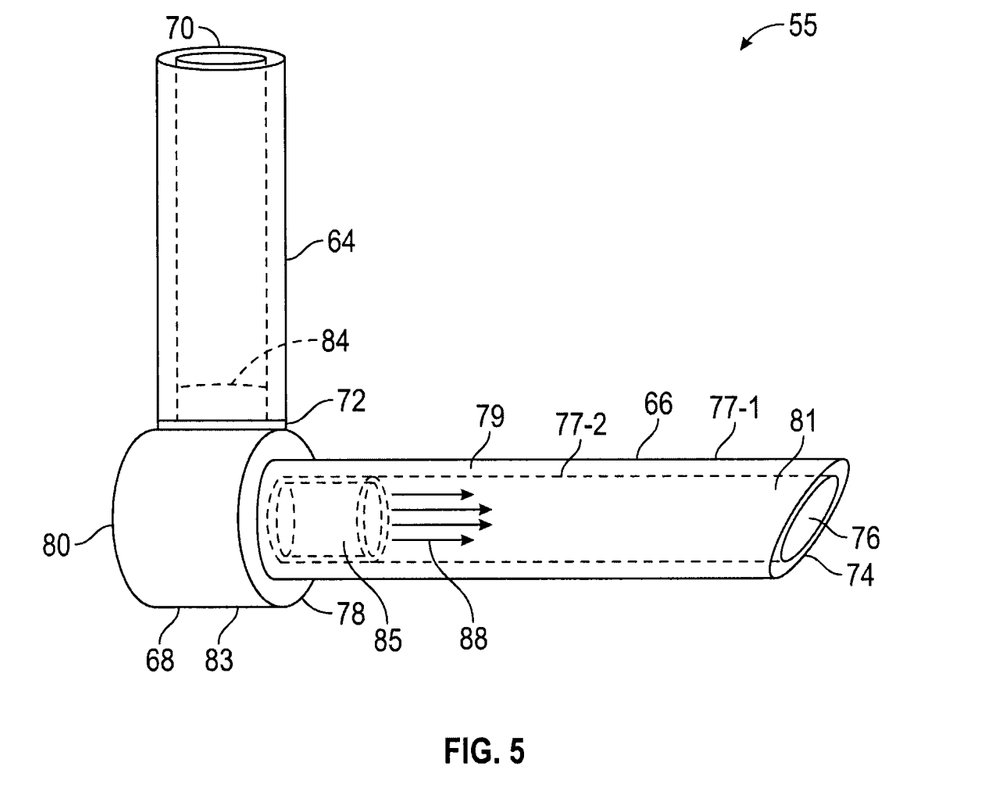
FIG. 5 is a partial cutaway view of a laryngoscope included with the kit of FIG. 4, in some embodiments of the present disclosure.

Referring now to FIGS. 4, 5, 5-1, and 5-2, the laryngoscope 55 may be implemented as any laryngoscope suitable to aid in the placement of the bougie 10 through the mouth 12 and into the trachea 20 of the patient 14, including standard curved blade laryngoscopes. In some embodiments, the laryngoscope 55 may include a handle assembly 64, a cylindrical tube 66, and an optical subassembly 68 extending between the handle assembly 64 and the cylindrical tube 66. The cylindrical tube 66, the handle assembly 64, and the optical subassembly 68 can be a unitary construction or of separate construction as shown in FIG. 5-1. Further, the cylindrical tube 66, the handle assembly 64, and the optical subassembly 68 may be constructed of a disposable material, such as metal, plastics, Silastic® (available from Dow Corning®, Midland, Mich., U.S.A.), pyrex (glass) (Corning inc) polytetrafluoroethylene, polyethylene terephthalate (PET), polyvinyl chloride (PVC), polyethylene (PE), polybutylene terephthalate (PBT), or other suitable materials or combinations thereof, The handle assembly 64 may have a distal end 70 and a proximal end 72 which is removably secured to the optical subassembly 68. The handle assembly 64 may have a bent configuration or a straight configuration as illustrated in FIG. 4.

The cylindrical tube 66 may have a distal end 74 having a distal end opening 76 and a proximal end 78 having a proximal end opening 80. The proximal end 78 may be removably secured to the optical subassembly 68. The distal end opening 76 may be oriented at an angle relative to a vertical cross sectional plane of the cylindrical tube 66. The angling of the distal end opening 76 may aid in the insertion of the cylindrical tube 66 into the patient's 14 mouth 12 and throat. The cylindrical tube 66 may have an outer surface 77-1 and an inner surface 77-2 with a thickness 79 therebetween. The inner surface 77-2 may define an open passage, known as a lumen 81, which extends the length of the cylindrical tube 66. The distal end opening 76 may provide access to the lumen 81 and the proximal end opening 80 may also provide access to the lumen 81. As such, the cylindrical tube 66 may be hollow and allow the user to view inside the patient's 14 mouth 12 and throat.

The proximal end 78 of the cylindrical tube 66 may be secured to the proximal end 72 of the handle assembly 64. The connection of the cylindrical tube 66 and the handle assembly 64 may be of a unitary construction or of separate construction.

The cylindrical tube 66 may be rigid and may be made of a suitable metal, a transparent material, a translucent material, a disposable material, a non-translucent material, or combination thereof. The use of transparent and/or translucent material can aid with the illumination of the entire cylindrical tube 66 along its length, where the light 88 emanating from the end 90 of the light carrier 86 propagates into the translucent material to illuminate the entire cylindrical tube 66. This is useful in situations where blood or other items can hinder the ability to view the interior of the patient's 14 mouth 12 and/or throat. The laryngoscope 55 may be of different lengths and widths so long as the first, second, and third depth indicators 24, 26, and 51 take into account the length of the laryngoscope to accurately position the first end 16 or the second end 28 past the vocal cord 18 of the patient 14.

In some embodiments, the optical subassembly 68 may include a light source 82 located within the handle assembly 64, a power source 84 located within the handle assembly 64 and in communication with the light source 82. In some embodiments, the optical subassembly 68 may have a light source housing 83, which may be removably secured to the cylindrical tube 66 such that the outer surface of the optical subassembly 68 is continuous with the outer surface 77-1.

The optical subassembly 68 may have an opening 85 that extends the length of the optical subassembly 68 and that corresponds to the lumen 81. The opening 85 allows for the proper placement of the cylindrical tube 66. A user may peer into the opening 85 and look through the lumen 81 and through the distal end opening 76 to see inside the patient's 14 mouth 12 and trachea 20. The power source 84 may include known power sources including batteries. In some embodiments, a light carrier 86 may be included in the light source housing 83 or within the handle assembly 64 and may extend into the cylindrical tube 66. The light carrier 86 is in communication with the light source 82. The light carrier 86 may include fiber optic cables, light emitting diodes (LEDs), ring of light emitting diodes, or other light sources that may project sufficient light into and through the cylindrical tube 66. The light carrier 86 terminates within the cylindrical tube 66. Light 88 emanates from an end 90 of the light carrier 86. A first portion of the light 88 may exit an interior of the cylindrical tube 66 via the distal opening 76 and a second portion of the light 88 may propagate into the cylindrical tube 66 to illuminate the cylindrical tube 66, where the cylindrical tube 66 is made of a translucent material. The light 88 illuminates the interior of the cylindrical tube 66 thereby aiding the user of the laryngoscope 55 in placing the laryngoscope 55 within the mouth 12 and throat of the patient 14. Although shown as a circular light source 82, the light source 82 may be implemented in other configurations.

Figure 52:
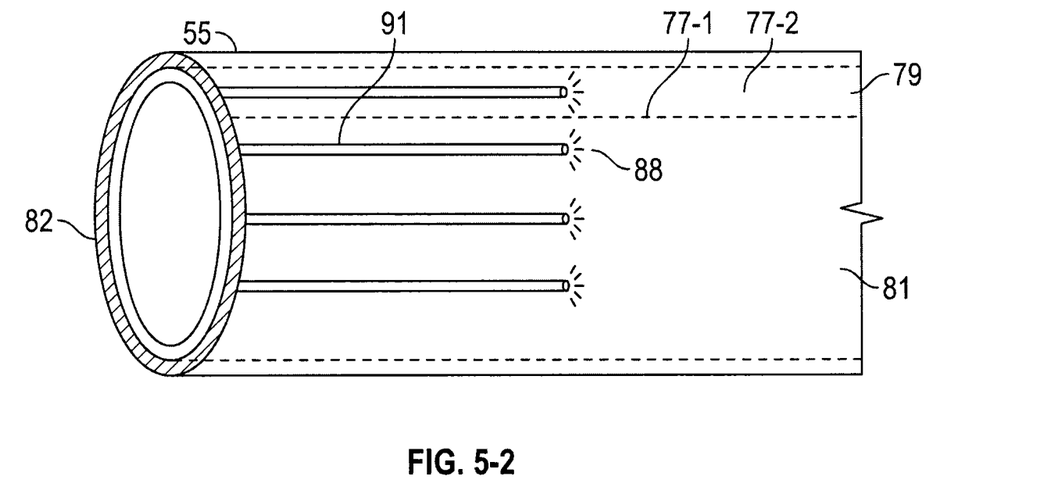

In some embodiments, the light source 82 may be located around the circumference of the cylindrical tube 66 at or near the proximal end 78. For example, the light source 82 may be a plurality of light sources 82 located at distinct points, separated a distance apart, along the circumference of the cylindrical tube 66. By way of further example, as shown in FIG. 5-2, fiber optic lines 91 may extend from the light source 82 or the plurality of light sources 82 and through the thickness 79 of the cylindrical tube 66 between the outer surface 77-1 and the inner surface 77-2. The fiber optic lines 91 allow light to illuminate the outer surface 77-1 and/or inner surface 77-2, along the lumen 81 and along the length of the cylindrical tube 66. In either event, the light 88 from the light source 82 may travel along the length of the cylindrical tube 66 illuminating the outer surface 77-1 and/or the inner surface 77-2 of the cylindrical tube 66. The light 88 may aid the user in visualizing the larynx despite obstructions such as blood and vomit. The light 88 may also illuminate the circumference of the lumen 81 of the cylindrical tube 66.

The laryngoscope 55 may be disposable (or single use), allowing its inclusion with the bougie 10 and a suction catheter into an emergency airway kit, such as the kit 60, to be used by emergency medical services inside as well as outside of a medical (hospital) facility.

In some embodiments, once the laryngoscope 55 is placed within the patient's 14 throat, various devices, including a suction tube or the bougie 10, may be inserted through the cylindrical tube 66 into the patient's 14 trachea 20. When the bougie 10 is inserted, the cylindrical tube 66 may then be removed by sliding the cylindrical tube 66 along the bougie 10, leaving the bougie 10 in place. The bougie 10 may then act as a guide for the placement of additional devices such as the endotracheal tube 56 to aid the patient 14.

Figure 6:
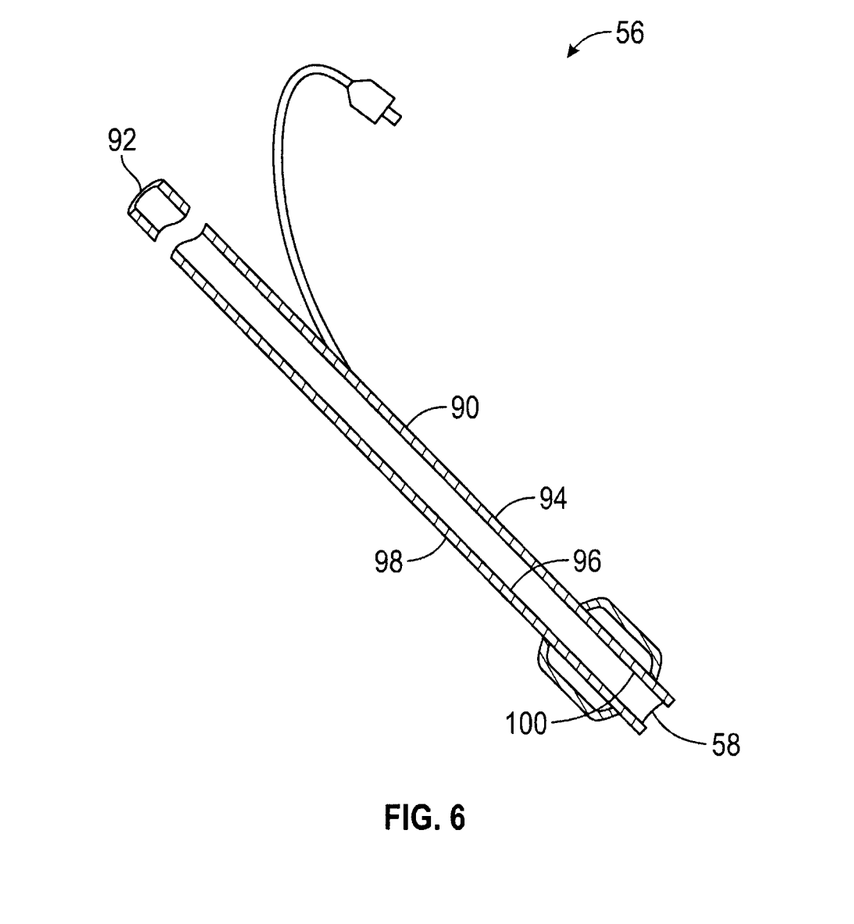
FIG. 6 is a side view of an endotracheal tube included with the kit of FIG. 4, in some embodiments of the present disclosure.

Referring now to FIGS. 4 and 6, in some embodiments, the kit 60 may additionally include the endotracheal tube 56. The endotracheal tube 56 may include a tubular member 90 with the first end 58, a second end 92, and a sidewall 94 extending between the first and second ends 58 and 92. The sidewall 94 may have an inner surface 96 and an outer surface 98. The inner surface 96 may define a void 100 sized and dimensioned to receive the body 22 of the bougie 10. The tubular member 90 may be constructed of a flexible and non-immunogenic material, such as those described above in relation to the bougie 10. In some embodiments, the endotracheal tube 56 may also be provided with an inflatable cuff proximate to the first end 58 and a side tube in fluid communication with the inflatable cuff which may be used to inflate and/or deflate the inflatable cuff.

Figure 7:
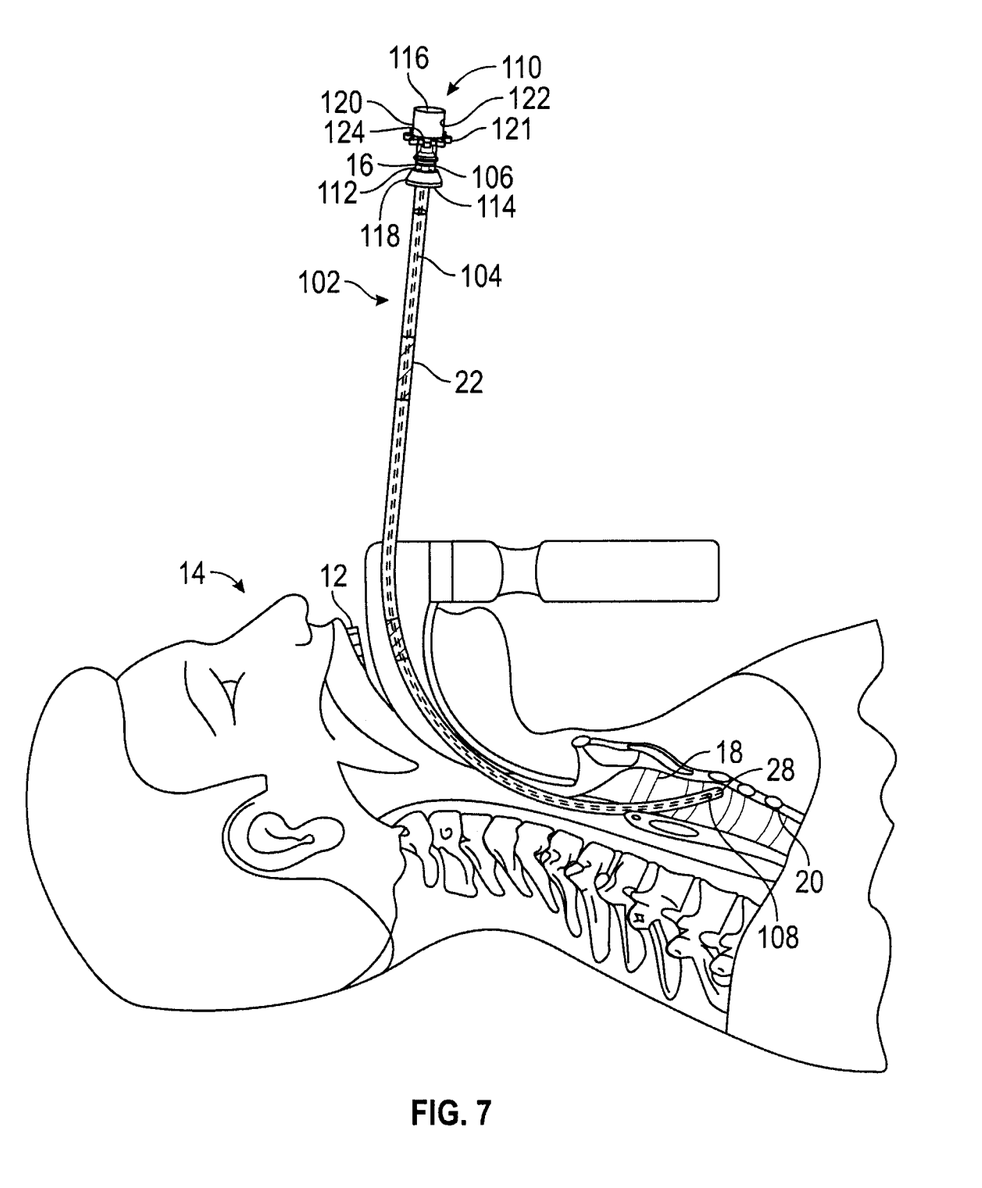
FIG. 7 is a partial cross sectional diagram of positioning a bougie into a trachea of a patient with an adapter connected to the bougie for ventilation of the patient.
Figure 31:
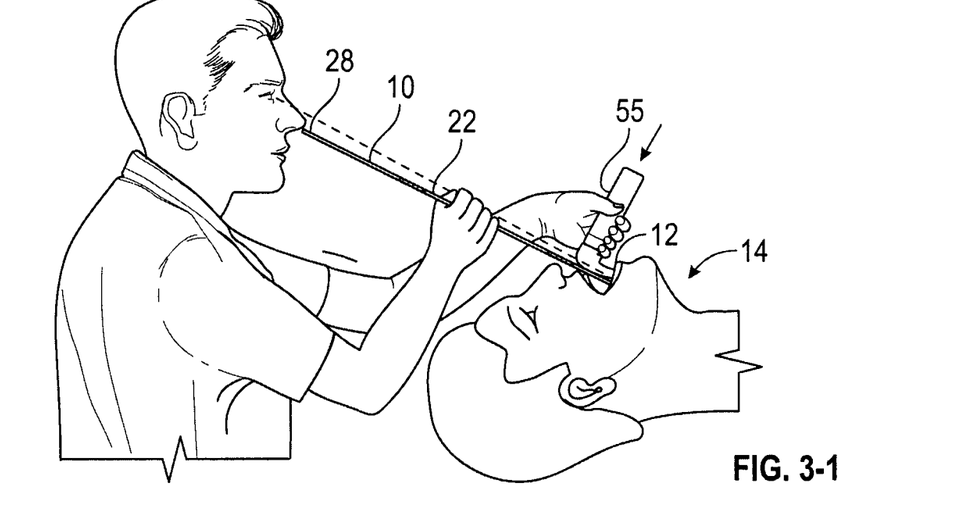
Figure 32:
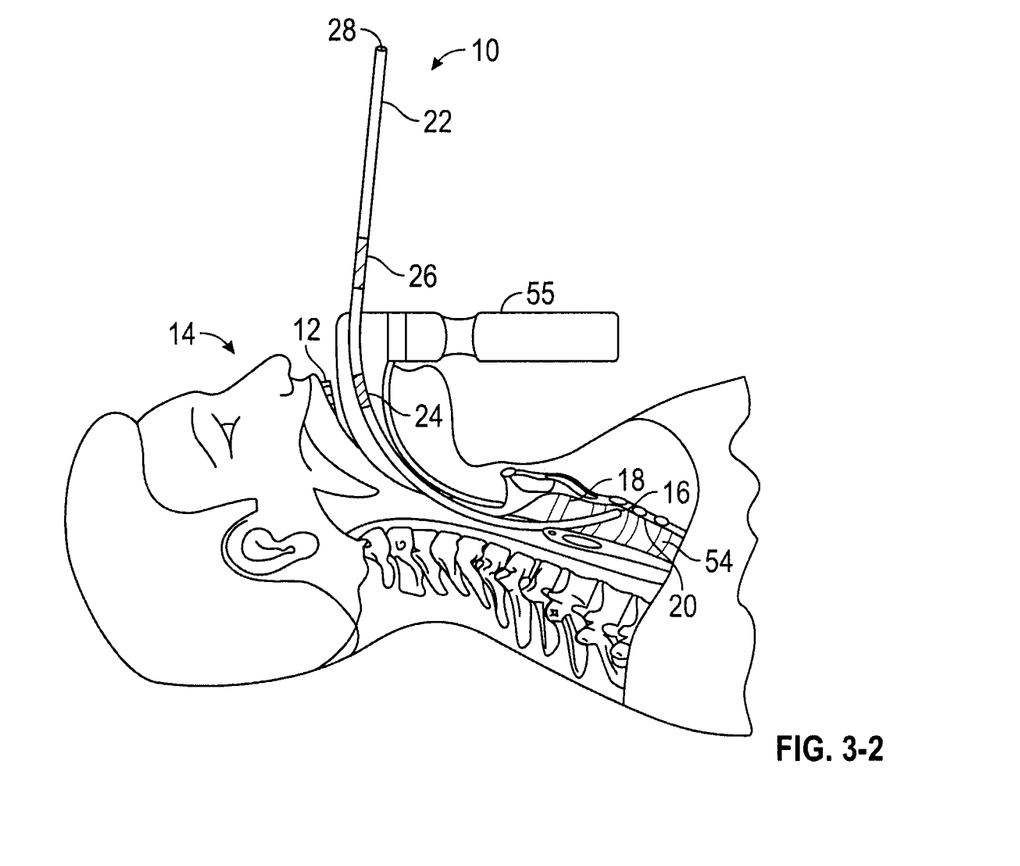
Figure 33:
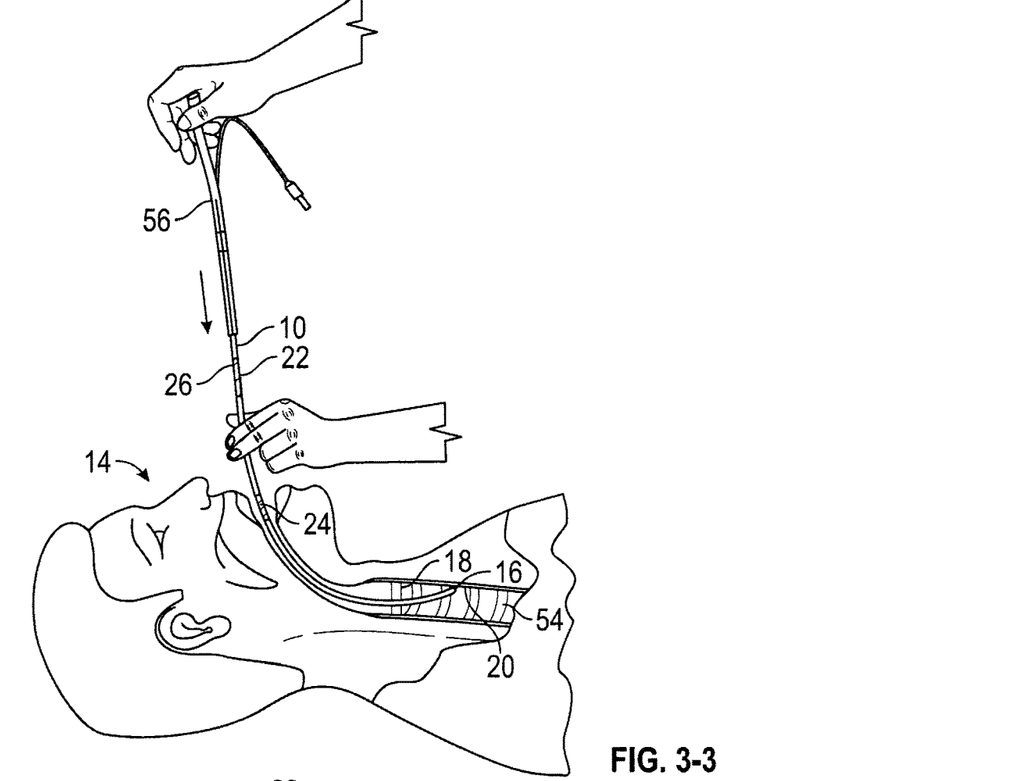
Figure 34:
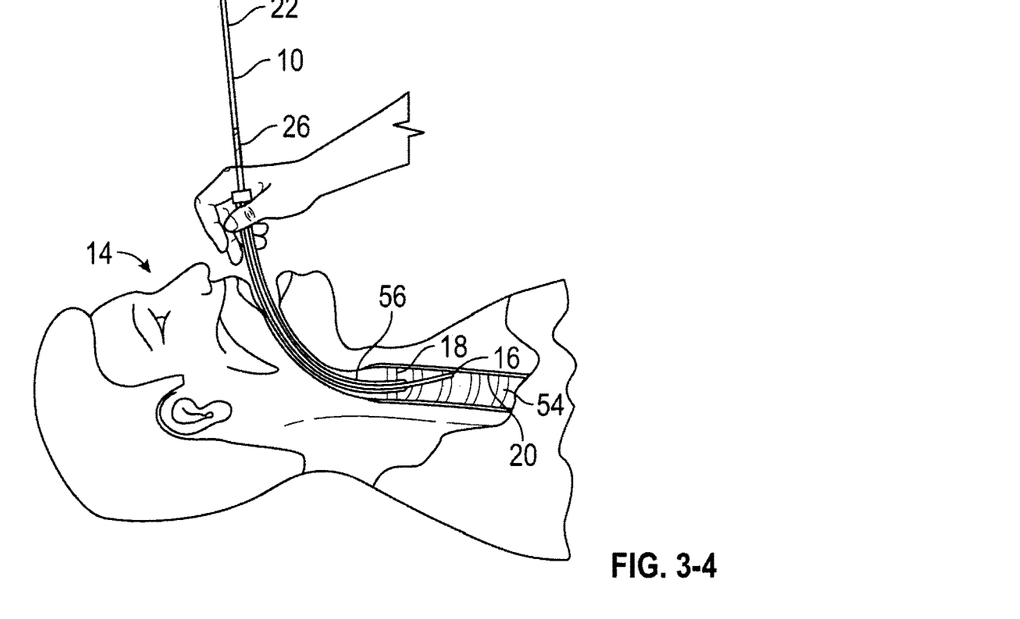
Figure 35:
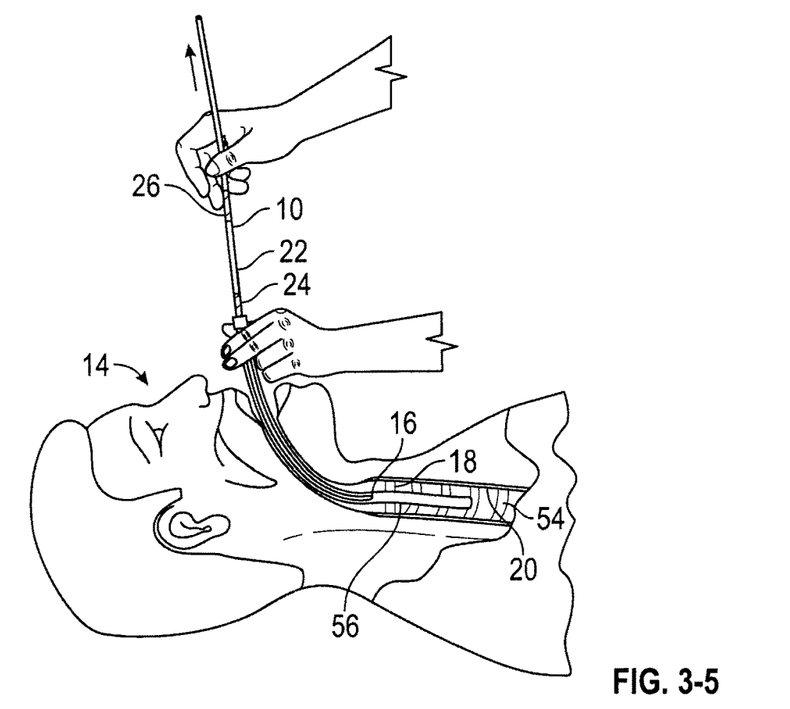
Figure 51:
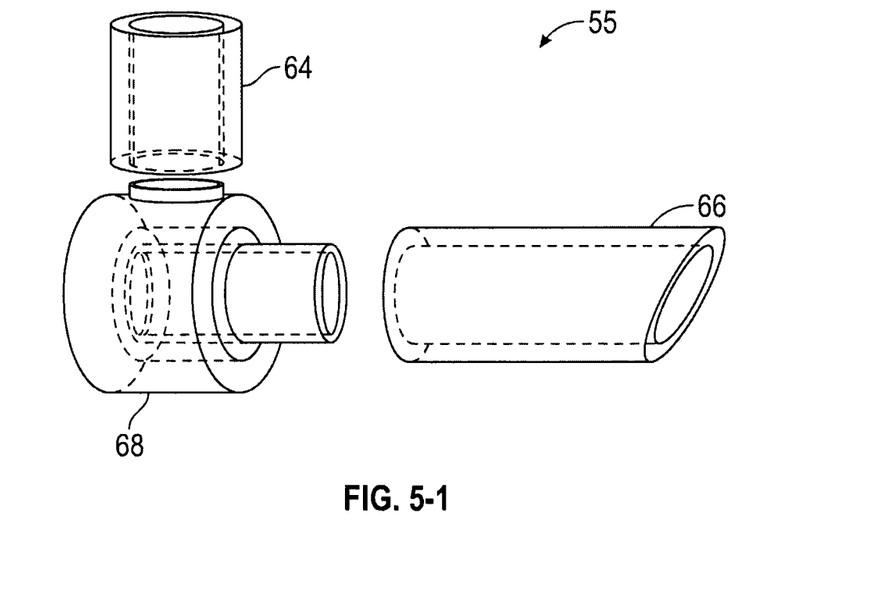

Referring now to FIG. 7, therein shown is a bougie 102, in accordance with some embodiments of the present disclosure. The bougie 102 may be used to assist in ventilation of the patient 14 where other options for ventilation are limited or unavailable. The bougie 102 may be implemented substantially similar to the bougie 10; however, the bougie 102 may additionally include a ventilation channel 104 extending between the first end 16 and the second end 28. The ventilation channel 104 may be defined by the body 22 with at least one first opening 106 proximate to the first end 16 and at least one second opening 108 proximate to the second end 28. The ventilation channel 104 may be sized and configured to enable ventilation of the patient 14 by air passage through the body 22 of the bougie 102. In some embodiments, the first end 16 or the second end 28 may additionally be configured to connect the bougie 102 to an intubation device or an air or other gas flow. For example, as shown in FIG. 7, the first end 16 may be configured to be connected to an anesthetic machine, a ventilation bag, or other device via an adapter 110.

The adapter 110 may include a body 112 having a first end 114 and a second end 116, a first connection member 118 proximate to the first end 114 of the body 112, a second connection member 120 proximate to the second end 116 of the body 112, and a shoulder 121 separating the first connection member 118 from the second connection member 120. The body 112 may also define a cavity 122 proximate to the second end 116 and extending from the shoulder 121 toward the second end 116. The adapter 110 may be formed from plastic, rubber, steel, or any other sterilizable material suitable for use in medical devices, similar to those described above. The material forming the adapter 110 may additionally be capable of enabling a sealing relationship between a ventilation device, the adapter 110, and the bougie 102, as will be explained in more detail below.

The first connection member 118 may be configured to receive the first end 16 of the bougie 102, so as to mechanically connect the first end 16 of the bougie 102 to the body 112 of the adapter 110. In some embodiments, the mechanical connection of the first connection member 118 may form a sealing relationship between the bougie 102 and the body 112 of the adapter 110. The second connection member 120 may be configured to mechanically connect a portion of a ventilation device to the body 112 of the adapter 110. The ventilation device may be an air flow hose, a respiratory ventilator, a fitting of a bag-valve mask ventilator, an anesthetic machine, or any other suitable ventilation device, for example. In some embodiments, the mechanical connection of the second connection member 120 may form a sealing relationship between the ventilation device and the body 112 of the adapter 110.

In some embodiments, first connection member 118 may be implemented as a luer lock, a friction fit, a threaded connection member, a clamp, or any other suitable mechanical connection mechanism. Similarly, the second connection member 120 may be a friction fit, a luer lock, a threaded connector, a clamp, or any other suitable mechanical connection mechanism. In at least some embodiments, the second connection member 120 is larger in diameter than the first connection member 118.

The shoulder 121 may function to limit a connection depth of the ventilation device to the body 112 to prevent the second end 116 from being inserted too far into the ventilation device. The shoulder 121 may also function to provide lateral support for the cavity 122 and the second connection member 120 in embodiments where the cavity 122 and the second connection member 120 are larger in diameter than the first end 114 and the first connection member 118.

The first end 114 and the second end 116 of the body 112 may be in fluid communication via a passage 124 such that the cavity 122 may receive air or other gasses from a ventilation device connected to the second connection member 120. The passage 124 may then allow transfer of the air or other gasses to the first end 114 of the body 112 and to the bougie 102 connected to the first connection member 118. As such, a gas flow path may be established from the ventilation device, through the adapter 110, into the at least one first opening 106 of the bougie 102, through the ventilation channel 104, and out of the at least one second opening 108 of the bougie 102. In this manner, the patient 14 may be ventilated via the combination of the ventilation device, the adapter 110, and the bougie 102 acting in cooperation.

In some embodiments, the adapter 110 may be included in a kit with the bougie 102. For example, the adapter 110 may be included in the kit 60 along with the bougie 102, the laryngoscope 55 and the endotracheal tube 56. In some embodiments, the kit 60 may include, along with the adapter 110 and the bougie 102, one or more suction catheter, and/or one or more tools or instruments for manipulating the larynx, as described above.

While the present disclosure has been described with a certain degree of particularity, it is manifest that many changes may be made in the details of construction and the arrangement of components without departing from the spirit and scope of this disclosure. It is understood that the disclosure is not limited to the embodiments set forth herein for purposes of exemplification, but is to be limited only by the scope of the attached claims, including the full range of equivalency to which each element thereof is entitled.

What is claimed is:

1. A bougie, comprising:
a body having a first end and a second end wherein said body is configured for interchangeable insertion thereof into a mouth of a patient such that either said first end and said second end of said body are each configured to be inserted into the mouth and trachea of the patient at the discretion of a user, each of said ends being blunted, at least one surface extending between the first and second ends, the body having an elongated shape and a defined cross section wherein said elongated shape and defined cross section has a width of at least 8 Fr, and are sized and dimensioned to (i) pass either one of the first end or the second end through the mouth and into a trachea of the patient without causing trauma to the patient and after insertion to (ii) guide placement of an endotracheal tube there over into the trachea and after placement of said endotracheal tube there over to (iii) be safely removed whereby said endotracheal tube can aid in oxygenation of the patient, the body being constructed of a flexible and non-immunogenic material, the body having a longitudinal axis extending between the first end and the second end;

a first insertion depth range indicator on the body, the first insertion depth range indicator indicating a first predetermined insertion depth range, the first insertion depth range indicator having a first end spaced a first distance from the first end of the body, and indicative of a first minimum insertion depth of the first predetermined insertion depth range, and a second end being indicative of a maximum insertion depth of the first predetermined insertion depth range, the first insertion depth range and the first distance being based upon an analysis of a first subset of patients within a group of all possible patients;

a second insertion depth range indicator on the body, the second insertion depth range indicator indicating a second predetermined insertion depth range different from the first predetermined insertion depth range, the second insertion depth range indicator having a first end spaced a second distance from the second end of the body and indicative of a second minimum insertion depth of the second predetermined insertion depth range, and a second end being indicative of a maximum insertion depth of the second predetermined insertion depth range, the first distance being different from the second distance, the second insertion depth range, and the second distance being based upon an analysis of a second subset of patients within the group of all possible patients; and wherein the first and second insertion depth range indicators are substantially continuous, elongated along the longitudinal axis, and visually distinguished parts of the body relative to a region between the first and second insertion depth range indicators.

2. The bougie of claim 1, wherein the first predetermined insertion depth range is sized for insertion past the mouth and into the airway of the patient of a first predetermined age range.

3. The bougie of claim 2, wherein the second predetermined insertion depth range is sized for insertion past the mouth and into the airway of the patient of a second predetermined age range.

4. The bougie of claim 1, wherein the first insertion depth range indicator is selected from a group consisting of a raised section, a lowered section, a textured section, and a colored section.

5. The bougie of claim 1, wherein the first predetermined insertion depth range is between 23 cm and 33 cm.

6. The bougie of claim 1, wherein the second insertion depth range indicator is selected from a group consisting of a raised section, a lowered section, a textured section, and a colored section.

7. The bougie of claim 1, wherein the second predetermined insertion depth range is between 23 cm and 33 cm.

8. The bougie of claim 1, further comprising a third insertion depth range indicator positioned on the body of the bougie between the first insertion depth range indicator and the second insertion depth range indicator.

9. The bougie of claim 1, wherein the region between the first and second insertion depth range indicators has a longitudinal length greater than the first distance and the second distance.

10. The bougie of claim 1 wherein the first insertion depth range indicator has markings, and wherein the region between the first and second insertion depth range indicators has a blank area having a longitudinal length greater than any spacing between the markings.

11. The bougie of claim 10, wherein the markings are contrasting areas indicative of discrete measurements.

12. A kit, comprising:
  a bougie, comprising:
    a body having a first end and a second end wherein said body is configured for interchangeable insertion thereof into a mouth of a patient such that either said first end and said second end of said body are each configured to be inserted into the mouth and trachea of said patient at the discretion of a user, each of said ends being blunted, at least one surface extending between the first and second ends, the body having an elongated shape and a defined cross section wherein said elongated shape and defined cross section are sized and dimensioned to (i) pass either one of the first end or the second end through the mouth and into the trachea of the patient without causing trauma to the patient and after insertion to (ii) guide placement of an endotracheal tube there over into the trachea and after placement of said endotracheal tube there over to (iii) be safely removed whereby said endotracheal tube can aid in oxygenation of the patient, the body being constructed of a flexible and non-immunogenic material, the body having a longitudinal axis extending between the first end and the second end;
    a first insertion depth range indicator on the body the first insertion depth range indicator indicating a first predetermined insertion depth range, the first insertion depth range indicator having a first end spaced a first distance from the first end of the body, and indicative of a first minimum insertion depth of the predetermined insertion depth range, and a second end being indicative of a maximum insertion depth of the predetermined insertion depth range, the first insertion depth range and the first distance being based upon an analysis of a first subset of patients within a group of all possible patients;
    a second insertion depth range indicator on the body the second insertion depth range indicator indicating a second predetermined insertion depth range different from the first predetermined insertion depth range, the second insertion depth range indicator having a first end spaced a distance from the second end of the body and indicative of a second minimum insertion depth of the second predetermined insertion depth range, and a second end being indicative of a maximum insertion depth of the second predetermined insertion depth range, the first distance being different from the second distance, the second insertion depth range and the second distance being based upon an analysis of a second subset of patients within the group of all possible patients;
    wherein the first and second insertion depth range indicators are substantially continuous, elongated along the longitudinal axis, and visually distinguished parts of the body relative to a region extending between the first and second insertion depth range indicators; and
  a laryngoscope, comprising:
    a handle;
    a tube constructed of a translucent material and having a proximal end coupled with the handle, a distal end including a distal opening, and an interior extending from the proximal end of the distal end; and
    an optical subassembly providing light into the interior of the tube so that a first portion of the light exits the interior of the tube via the distal opening and a second portion of the light propagates into the translucent material to illuminate the tube.

13. The kit of claim 12 further including an endotracheal tube having a tubular member with a first end, a second end, and a sidewall extending between the first and second ends, the sidewall having an inner surface and an outer surface with the inner surface defining void sized and dimensioned to receive the body of the bougie, the tubular member being constructed of a flexible and non-immunogenic material.

14. The kit of claim 12, wherein the first predetermined depth range is sized for insertion past the mouth and into the airway of the patient of a first predetermined age range.

15. The kit of claim 12, wherein the second predetermined depth range is sized for insertion past the mouth and into the airway of the patient of a second predetermined age range.

16. The kit of claim 12, wherein the first depth indicator is selected from a group consisting of a raised section, a lowered section, a textured section, and a colored section.

17. The kit of claim 12, wherein the second depth indicator is selected from a group consisting of a raised section, a lowered section, a textured section, and a colored section.

18. The kit of claim 12, wherein the bougie further comprises a third insertion depth range indicator positioned on the body of the bougie between the first insertion depth range indicator and the second insertion depth range indicator.

* * * * *

UNITED STATES PATENT AND TRADEMARK OFFICE
CERTIFICATE OF CORRECTION

PATENT NO. : 11,547,823 B2
APPLICATION NO. : 14/251296
DATED : January 10, 2023
INVENTOR(S) : Nilesh R. Vasan It is certified that error appears in the above-identified patent and that said Letters Patent is hereby corrected as shown below:

On the Title Page

Under (73) Assignee: Insert -- Adroit Surgical, LLC, Oklahoma City, OK --

Signed and Sealed this
Eleventh Day of April, 2023

Katherine Kelly Vidal
*Director of the United States Patent and Trademark Office*